United States Patent [19]

Dupont et al.

[11] Patent Number: 4,563,174

[45] Date of Patent: Jan. 7, 1986

[54] DEVICE FOR MIXING SEVERAL COMPONENTS

[76] Inventors: Philippe Dupont, 3 rue Colbert, Clermont-Ferrand, Puy-de-Dome; Jean Lontrade, 124 avenue Thermale, Chamalieres, Puy-de-Dome, both of France

[21] Appl. No.: 470,972

[22] Filed: Feb. 28, 1983

Related U.S. Application Data

[63] Continuation-in-part of Ser. No. 466,343, filed as PCT FR 82/00111, Jun. 29, 1982, § 102(e) date Feb. 7, 1983, abandoned.

[30] Foreign Application Priority Data

Jun. 29, 1981 [FR] France .................................. 81 13193

[51] Int. Cl.[4] .............................................. A61M 5/18
[52] U.S. Cl. ..................................................... 604/89
[58] Field of Search .................... 604/89, 90, 82, 92

[56] References Cited

U.S. PATENT DOCUMENTS

| 3,330,280 | 7/1967 | Ogle | 604/89 |
| 3,342,180 | 9/1967 | Sandhage et al. | 604/89 |
| 3,835,855 | 9/1974 | Barr, Jr. | 604/89 |

Primary Examiner—John D. Yasko
Attorney, Agent, or Firm—Karl F. Ross; Herbert Dubno

[57] ABSTRACT

A device for mixing two components, at least one of them a liquid, has a barrel with a wide-open end receiving a tubular plunger having an extremity open toward the barrel. The plunger is provided at that extremity with a relatively rotatable plug, fitting slidably into the open barrel end, and forms an outlet for the contents of that plunger which can be opened or closed by such relative rotation whereby the plug/plunger assembly can be filled with one component and sealed before being introduced from above into the barrel loaded with the other component. Either the plug or the plunger consists of elastic material and the plunger or the barrel may be provided with a sealable discharge opening which can be fitted with a needle when the device is to be used as a syringe.

3 Claims, 9 Drawing Figures

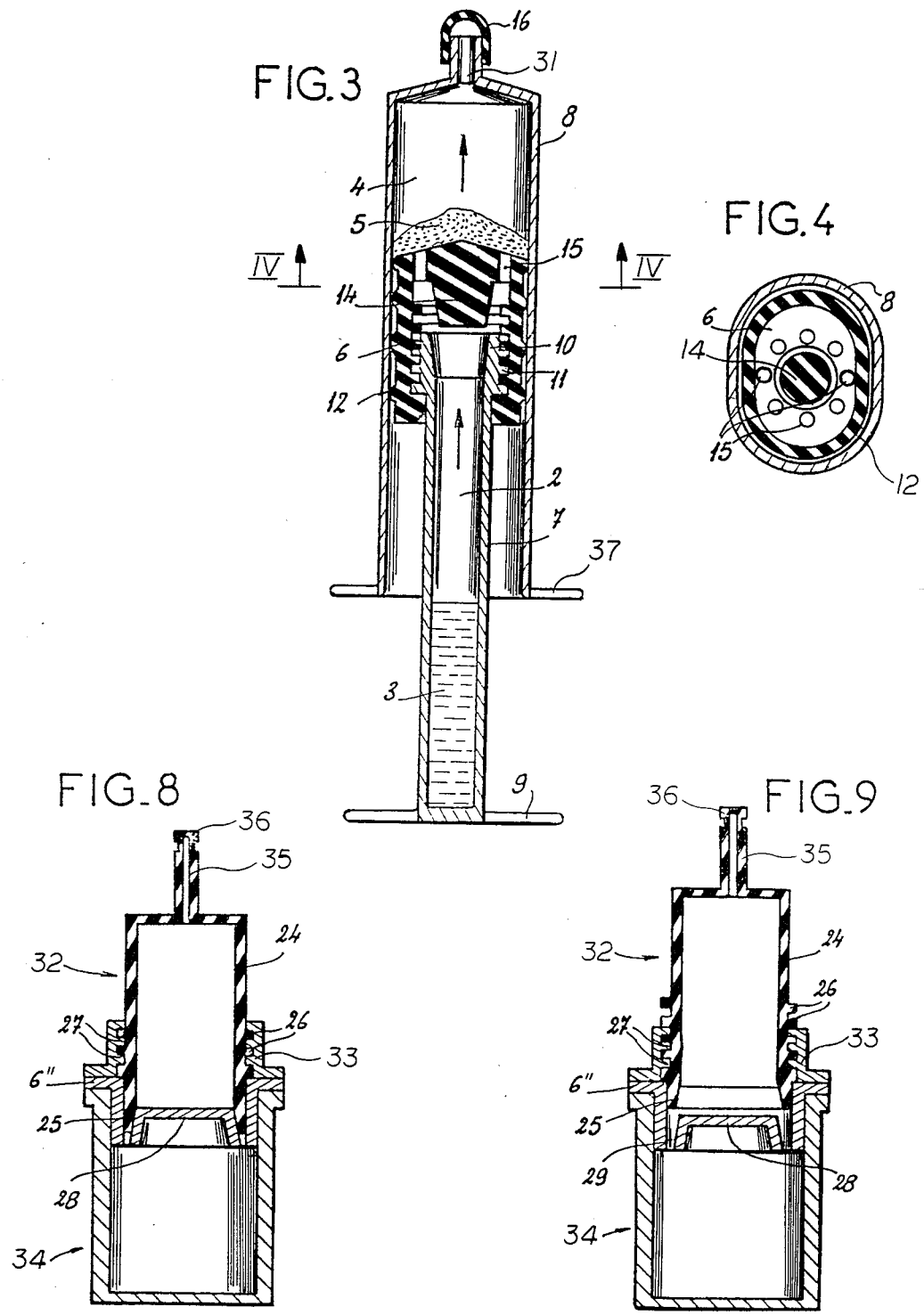

DEVICE FOR MIXING SEVERAL COMPONENTS

CROSS REFERENCE TO RELATED APPLICATIONS

This application is a continuation-in-part of our co-pending application Ser. No. 466,343 filed as PCT FR 82/00111, Jun. 29, 1982, § 102(e) date Feb. 7, 1983 (now abandoned) as a national phase application corresponding to the international application PCT/FR 81/00111 filed June 29, 1982 and based upon the French application No. 81 13 193 of June 29, 1981 under the International Covention.

FIELD OF THE INVENTION

Our present invention relates to a device, e.g. a syringe, designed to store two or possibly more components of a medication or of some other composition which are to be held separated before being jointly dispensed.

BACKGROUND OF THE INVENTION

The need for mutually isolating such components until just before their use, e.g. because of an instability of their mixture or for better preserving their sterility, has led to the development of syringes with two or more telescoped and relatively slidable constituents such as an outer barrel and a tubular plunger forming respective compartments for these components. Thus, U.S. Pat. No. 3,052,239 describes a disposable hypodermic syringe wherein an elastic valve head has an imperforate wall adapted to be stretched about an apertured piston head of a plunger to seal the interior thereof against the compartment formed in the outer barrel. U.S. Pat. No. 3,489,147 shows a gasket normally closing the compartment of the outer barrel, this gasket being pierceable by a needle on the plunger to establish communication between the plunger compartment and the barrel compartment. According to U.S. Pat. No. 3,680,558, a multicompartment syringe has a valve which can be opened or closed by a slight rotation of a plunger relative to an outer barrel.

In such syringes, or other mixing devices of this general type, the filling of the several compartments with their respective ingredients sometimes becomes a problem. Especially when one of the components of the mixture to be dispensed is a liquid, that liquid will have to be securely retained in its compartment for an extended period while the device is being assembled or while the remaining compartment or compartments are being filled. Often, moreover, another component of the mixture must be quickly sealed in its compartment to prevent prolonged exposure to the atmosphere; this may create additional difficulties of assembly.

OBJECTS OF THE INVENTION

The general object of our present invention, therefore, is to provide an improved mixing device of simple structure adapted to hold at least two ingredients, forming components of a mixture to be dispensed, in isolation from each other and from the environment for an idefinite period while allowing them to be quickly intermingled for joint discharge.

Another object is to provide means for enabling the retentin of such a component in a sealed unit separable from the remainder of the device while the latter is being cleaned or refilled with another component of the mixture.

SUMMARY OF THE INVENTION

We realize these objects in accordance with our present invention by providing a first tubular member with a wide-open end, forming a receptacle for a first component, and a second tubular member which forms a receptacle for a second component and has an open extremity projecting into that wide-open end in the assembled state of the device. A plug is slidably but nonrotatably fitted into the wide-open end of the first member and engages the inserted extremity of the second member with which it forms an outlet for the second component, this outlet being closable by relative rotation of the plug and the second member. The latter member and the plug together constitute the sealable unit which is bodily withdrawable from the first tubular member for filling with the second component and closure of the outlet prior to reintroduction into the first tubular member which meanwhile could have been filled with the first component.

Advantageously, at least one of the constituents of the sealable unit—i.e. the plug and/or the second tubular member—consists of elastic material in order to facilitate the interfitting of these two constituents after the second member has been filled with the respective component, usually a liquid. In principle, however, either member could be filled through a sealable discharge opening remote from the wide-open end of the first member, e.g. through a nipple to which an injection needle can be fitted when the device is to be used as a syringe.

BRIEF DESCRIPTION OF THE DRAWING

The above and other features of our present invention will now be described in detail with reference to the accompanying drawing in which:

FIG. 3 is a view similar to that of FIG. 2 but showing the establishment of communication between the interiors of the two tubular members;

FIG. 4 is a cross-sectional view taken on the line IV—IV of FIG. 3;

FIG. 8 is another cross-sectional view similar to that of FIG. 2 but relating to a further embodiment; and FIG. 9 is a view similar to that of FIG. 8 but showing the device in its communication-establishing position.

SPECIFIC DESCRIPTION

Figure 1:
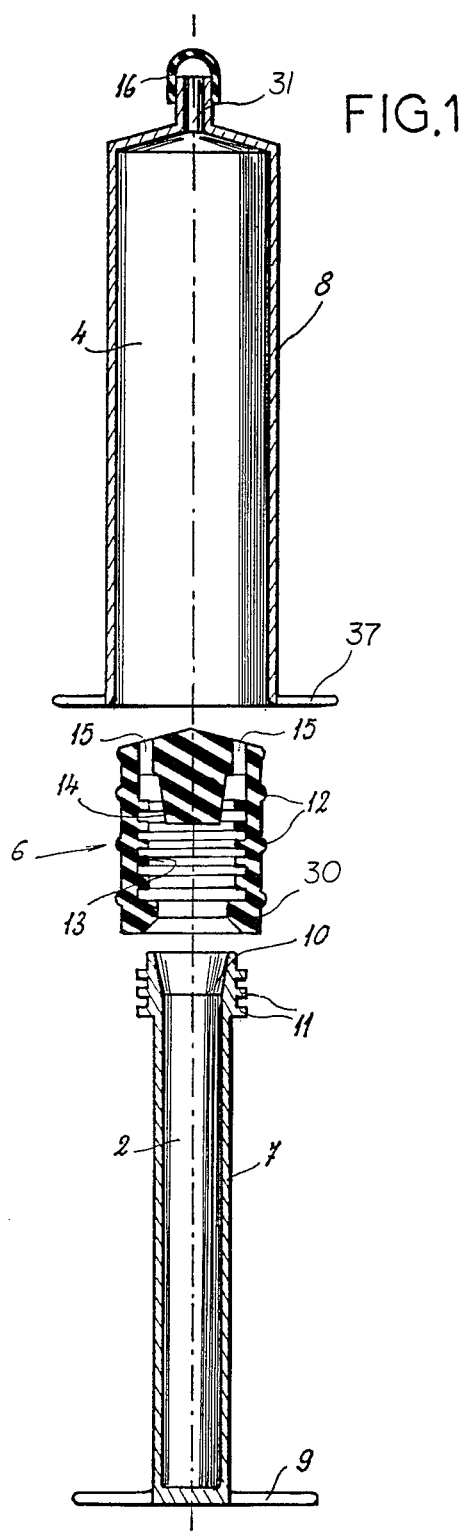
FIG. 1 is an exploded axial section view of a syringe-type mixing device according to our invention, including two tubular members and a plug.
Figure 2:
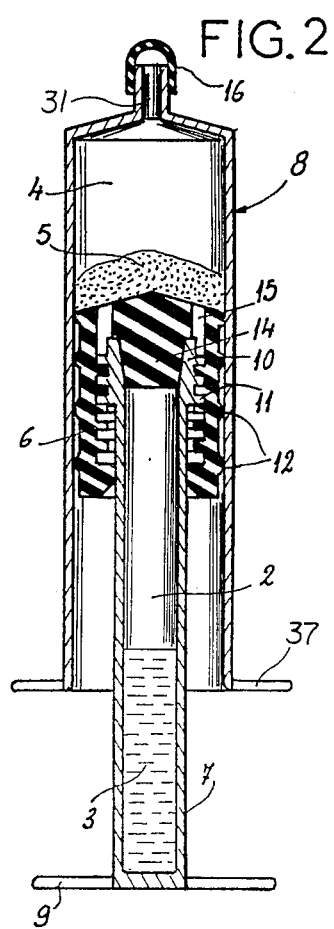
FIG. 2 is a view similar to FIG. 1, showing the device in its assembled state but with the interiors of the two tubular members sealed against each other by the plug.

We shall first refer to FIGS. 1-4 showing a syringe with a cylindrical outer barrel 8 constituting a first tubular member, a plunger 7 constituting a second tubular member, and a plug 6 of elastic material with outer ribs fitting closely into the interior 4 of barrel 8. The interior 2 of plunger 7 is closed at one end while being frustoconically flared at an opposite extremity 10 designed to embrace a complementarily tapering boss 14 projecting inward from an end wall of plug 6 having apertures 15. Female threads 13 on the peripheral wall of plug 6 mate with male threads 11 on plunger extremity 10, the plug also having an internal annular shoulder 30 preventing an accidental separation of parts 6 and 7 from each other after they have been resiliently interfitted as shown in FIGS. 2 and 3. As seen in FIG. 4, barrel 8 and plug 6 have mutually complementary noncircular cross-sections (substantially elliptical in this instance) which prevent their relative rotation in the assembled position of FIGS. 2-4; plunger 7, however, can be rotated in that position relatively to plug 6 for selectively blocking or unblocking the outlet apertures 15 through which the constant-volume compartment 2 of plunger 7 communicates with the variable-volume compartment 4 of barrel 8 upon the axial withdrawal of extremity 10 from boss 14 as illustrated in FIG. 3. Such rotation is facilitated by lateral prongs 9 on the closed end of plunger 7 which, together with similar prongs 37 at the wide-open end of barrel 8, also enable the plunger to be axially displaced relatively to the barrel by the fingers of a user. A nipple 31 at the free end of barrel 8 forms a discharge aperture sealable by a cap 16.

In FIGS. 2 and 3 the compartment 2 of plunger 7 is partly filled with a liquid 3 while the compartment 4 of barrel 8 contains a mass of granular powder 5 to be mixed with the liquid for joint dispensation through the nipple 31 and a nonillustrated needle to be fitted onto same. While the powder 5 could be introduced into compartment 4 through the nipple 31, it will generally be more convenient to keep the nipple sealed and to load the powder into the inverted barrel through its wide-open end. The liquid 3 may have been previously introduced into the compartment 2 of the plunger 7 which is thereafter fitted with the plug 6 and screwed into its outlet-closing position (FIG. 2) outside the barrel. With the liquid 6 thus sealed within the detachable unit 6, 7, that unit is then inserted from above into the open end of barrel 8 whereupon the ingredients 3 and 4 can be held isolated from each other and from the surrounding atmosphere up to the time that a patient is to be injected with the mixture. Prior to such injection, of course, the syringe with its apertures 15 unblocked will have to be inverted from the position of FIG. 3 to let the liquid 3 enter the compartment 4; if the walls of plunger 7 and barrel 8 are made transparent and provided with scale graduations, a measured quantity of the liquid could be admitted into the powder compartment 4 whereupon the apertures 15 could be reblocked to retain the remainder of the liquid in compartment 2 while the mixture in compartment 4 is being injected. Unit 6, 7 can then be withdrawn from barrel 8 for a cleaning and refilling of compartment 4 preparatorily to a repetition of the previous steps; if the plunger initially contains enough liquid, this procedure could be reiterated several times.

Figure 5:
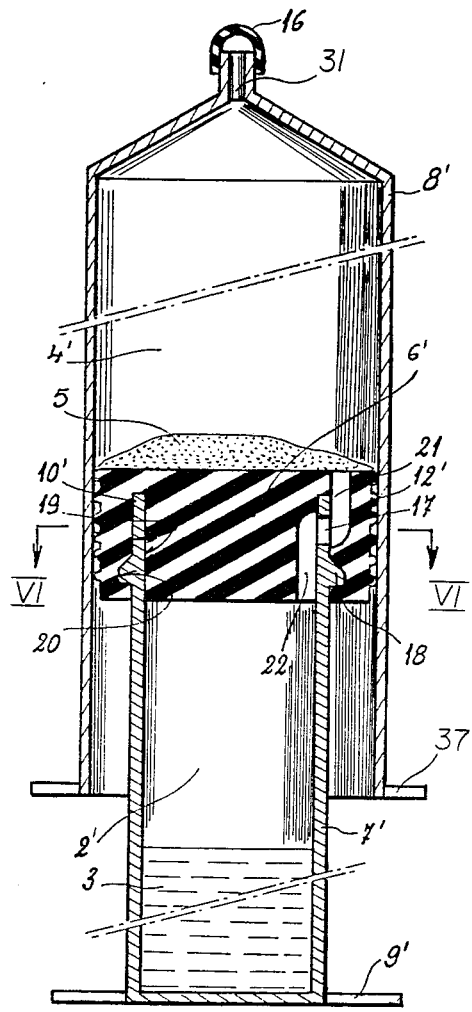
FIG. 5 is an axial sectional view similar to that of FIG. 2, showing a modified plug.
Figure 6:
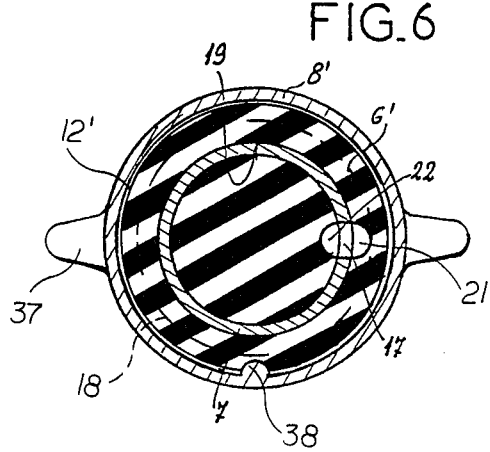
FIG. 6 is a cross-sectional view taken on the line VI—VI of FIG. 5, showing the plug in a communication-establishing position.
Figure 7:
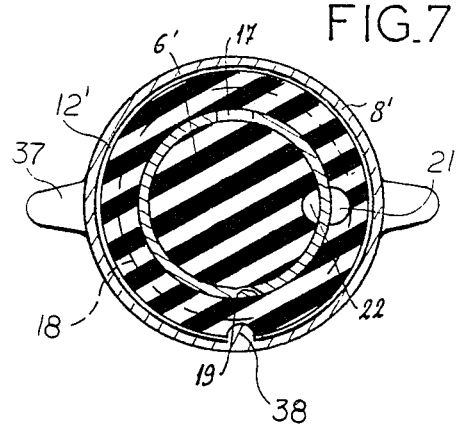
FIG. 7 is a cross-sectional view similar to that of FIG. 6 but showing the plug in a closure position.

The embodiment of FIGS. 5-7 differs from that of FIGS. 1-4 mainly in the provision of a modified plug 6' and plunger 7' with liquid compartment 2'; an associated barrel 8', with powder compartment 4', is shown to be of circular rather than elliptical cross-section, as are the plug 6' and the plunger 7'. A relative rotation of the barrel and the plug, however, is prevented in this instance by an axially extending inner rib 38 of barrel 8' mating with a complementary groove in the outer surface of plug 6'. The extremity 10' of plunger 7', remote from its closed end provided with prongs 9', is received in an annular groove 19 of plug 6' terminating short of the face of that plug which bounds the compartment 4'. Plug 6' is again closely fitted into the interior of barrel 8', through the intermediary of peripheral ribs 12', and its groove 19 is provided with an annular undercut 20 receiving a peripheral rib 18 on plunger 7' to prevent any untimely disassembly of the plug and the plunger from each other. Two passages 21 and 22 in plug 6', terminating at the outer and at the inner peripheral surface of groove 19, open into compartments 4' and 2', respectively. In the relative position of plug 6' and plunger 7' shown in FIGS. 5 and 6, passages 21 and 22 communicate with each other through a lateral port 17 of plunger extremity 10' so that liquid 3 from compartment 2' can pass into compartment 4' to mix with the powder 5. In the closure position of FIG. 7, port 17 is offset by about 90° from passages 21 and 22 whereby the two compartments are sealed against each other.

In FIGS. 8 and 9 we have shown another mixing device with a plunger 32, a barrel 34 and a plug 6"; this plug is rigid with an extension 33 having female threads 27 in mesh with male threads 26 on the peripheral wall 24 of plunger 32. The plunger, which in this instance consists of elastomeric material, has a nipple 35 sealable by a cap 36; its extremity 25 remote from that cap has a flared inner surface embracing a frustoconical boss 28 of plug 6" in a manner similar to that described with reference to extremity 10 and boss 14 of FIGS. 1-4. FIG. 8 shows the device in its closure position, separating the interior of plunger 32 from that of barrel 34, whereas in the position of FIG. 9 these compartments communicate with each other through apertures 29 in an end wall of the plug. Elements 32, 33, 6" again form a detachable unit which, after filling with a suitable ingredient, is slidably fitted into the wide-open end of barrel 34 for subsequent mixture of its contents with those of the barrel. The mixture, again, can be discharged through the uncapped nipple 35.

It will be apparent that the embodiments of FIGS. 5-7 and FIGS. 8, 9 operate in essentially the same manner as that of FIGS. 1-4. A device conforming to any of these embodiments can, of course, be used as often as desired without the need for a replacement of any of its parts, inasmuch as there are no rupturable membranes or the like. Moreover, the plunger of such a device need not be closed at its outer end but could be provided there with a nipple or a filling aperture, for example. In fact, that end of the plunger ould also be opened wide to receive a third tubular member of smaller diameter containing a further component to be admixed with the others, e.g. by way of a valve-forming plug similar to the one shown at 6, 6' or 6".

We claim:
1. A device for mixing several components, comprising:
 a first tubular member forming a receptacle for a first component and having a wide-open end;
 a second tubular member forming a receptacle for a second component and having an open extremity projecting into said wide-open end; and
 a plug slidable but nonrotatably fitted into said wide-open end in engagement with said extremity, said plug forming with said extremity an outlet for said second component closable by relative rotation of said plug and said second tubular member, said plug and said second tubular member together constituting a sealable unit bodily withdrawable from said first tubular member for filling with said second component and closure of said outlet prior to reintroduction into said first tubular member, said plug having a body with an annular groove bounded by concentric inner and outer peripheral surfaces receiving said extremity therebetween, said outlet including two internal passages of said body respectively terminating at said peripheral surfaces and opening radially toward one another and communicating with each other through a lateral port formed in said extremity in a predetermined relative rotary position of said second tubular member, one of said passages being open axially to the interior of said first tubular member, the other of said passages being open axially to the interior of said second tubular member.

2. A device as defined in claim 1 wherein at least one of the constituents of said unit consists of elastic material.

3. A device as defined in claim 1 wherein one of said tubular members is provided with a sealable discharge opening remote from said wide-open end.

* * * * *